(12) United States Patent
Maddison

(10) Patent No.: US 6,453,750 B1
(45) Date of Patent: Sep. 24, 2002

(54) STRESS TESTING APPARATUS

(76) Inventor: Anthony Maddison, 29 Billington Road West, Ehuesthorpe, Leicester LE9 7SD (GB)

( * ) Notice: Subject to any disclaimer, the term of this patent is extended or adjusted under 35 U.S.C. 154(b) by 0 days.

(21) Appl. No.: 09/609,856

(22) Filed: Jul. 5, 2000

(51) Int. Cl.$^7$ ................................................. G01N 3/00
(52) U.S. Cl. .......................... 73/816; 73/788; 73/798; 73/794; 73/809
(58) Field of Search .......................... 73/816, 798, 794, 73/809

(56) References Cited

U.S. PATENT DOCUMENTS 4,686,860 A    8/1987  Liu ............................... 73/856

FOREIGN PATENT DOCUMENTS

| EP | 0 596 696 A1 | 5/1994 | ............ B21D/24/14 |
|---|---|---|---|
| GB |   223341 A * | 7/1993 | ............ G01N/3/04 |
| GB | 2 263 341 A | 7/1993 | ............ G01N/3/04 |
| JP |   0596696 A1 * | 11/1994 | ............ B21D/24/14 |

* cited by examiner

*Primary Examiner*—Benjamin R. Fuller
*Assistant Examiner*—Andre Allen
(74) *Attorney, Agent, or Firm*—Young & Basile, P.C.

(57) ABSTRACT

A stress testing apparatus includes a cylinder block 2 with twelve cylinders 4, each housing a piston 14. Hydraulic pressure is provided to each of the cylinders 4 by a common supply bore 6 for urging each piston 14 out of its respective cylinder 4. A stress testing device 16 is mounted over each cylinder 4 and piston 14. For tensile testing (see FIG. 3) of a specimen (X), a piston (14*a*) acts on the housing (28*a*) of the device (16*a*) through pins (26), to push the housing (28*a*) away from the cylinder block 2. The specimen X is mounted between the housing (28*a*) and the cylinder block 2. For compressive testing (see FIG. 4), of a specimen Y the housing (28*b*) is rigidly secured to the cylinder block 2, and the cylinder (14*b*) acts to compress the specimen Y between the housing (28*b*) and the cylinder block 2 through a shaft (22*b*).

10 Claims, 4 Drawing Sheets

STRESS TESTING APPARATUS

The invention relates to stress testing device mounting apparatus and in particular to apparatus for use in the in situ stress testing of materials. More particularly, the stress testing apparatus provides variable tensile and compressive loads for the in situ stress testing of materials.

GB-A-2263341 discloses a device for performing fatigue tests on materials. The device is capable, in different embodiments, of subjecting materials to tensile or compressive stresses. Previously, fatigue tests required large, bulky equipment which necessitated tests being carried out in the laboratory or in static outdoor test environments. Laboratory testing is limited in that there are certain "real life" conditions which are very difficult artificially to replicate. The device disclosed in GB-A-2263341 has because of its size and simplicity enabled fatigue tests to be carried out away from the laboratory in real life environments. For instance, structural bonding systems for vehicle applications have been tested by mounting the devices on working vehicles so as to expose the system to real life variations in temperature, humidity and mechanical stress. However, when a number of materials are to be tested, in the same environment, the number of devices involved may result in the mounting of the devices and connections to them becoming complex and problematic.

The invention provides apparatus for mounting a plurality of stress testing devices comprising a cylinder block including a plurality of cylinders, a plurality of pistons each housed in one of the cylinders, means for conveying pressurised fluid from a source to each piston and means for attaching each device to the cylinder block at a position which enables the device to interact with a respective one of the pistons.

The apparatus according to the invention enables a plurality of testing devices to be conveniently located in the same position in an in-situ testing environment without the need for complex or extensive associated connections: Each device may operate from a single source of pressurised hydraulic fluid. The apparatus may be adapted to mount any number of testing devices. The apparatus may be fully or partially submerged in a liquid environment if so desired.

Preferably, the devices are releasably attached to the cylinder block and may be released without significantly affecting the pressure of the fluid and therefore the operation of the remaining devices. Each piston may be arranged so as to be retained in its respective cylinder whether or not a device is mounted to interact with that piston and adequate sealing means provided to prevent hydraulic fluid leaking past the piston.

Further preferably, the pressure of the fluid is varied in a random manner. The variations may be produced by monitoring a random event and translating that random event into a pressure value. Alternatively, the pressure of the fluid could be varied in a regular fashion, for instance, with a pump operated on a sinusoidal cycle.

The devices may subject the specimens under test to tensile stresses, compressive stresses or a combination of the two. Devices of the type shown in GB-A-2263341 are particularly suited to use with the apparatus according to the invention.

The invention will now be described, by way of example, with reference to the following drawings in which.

Figure 1:
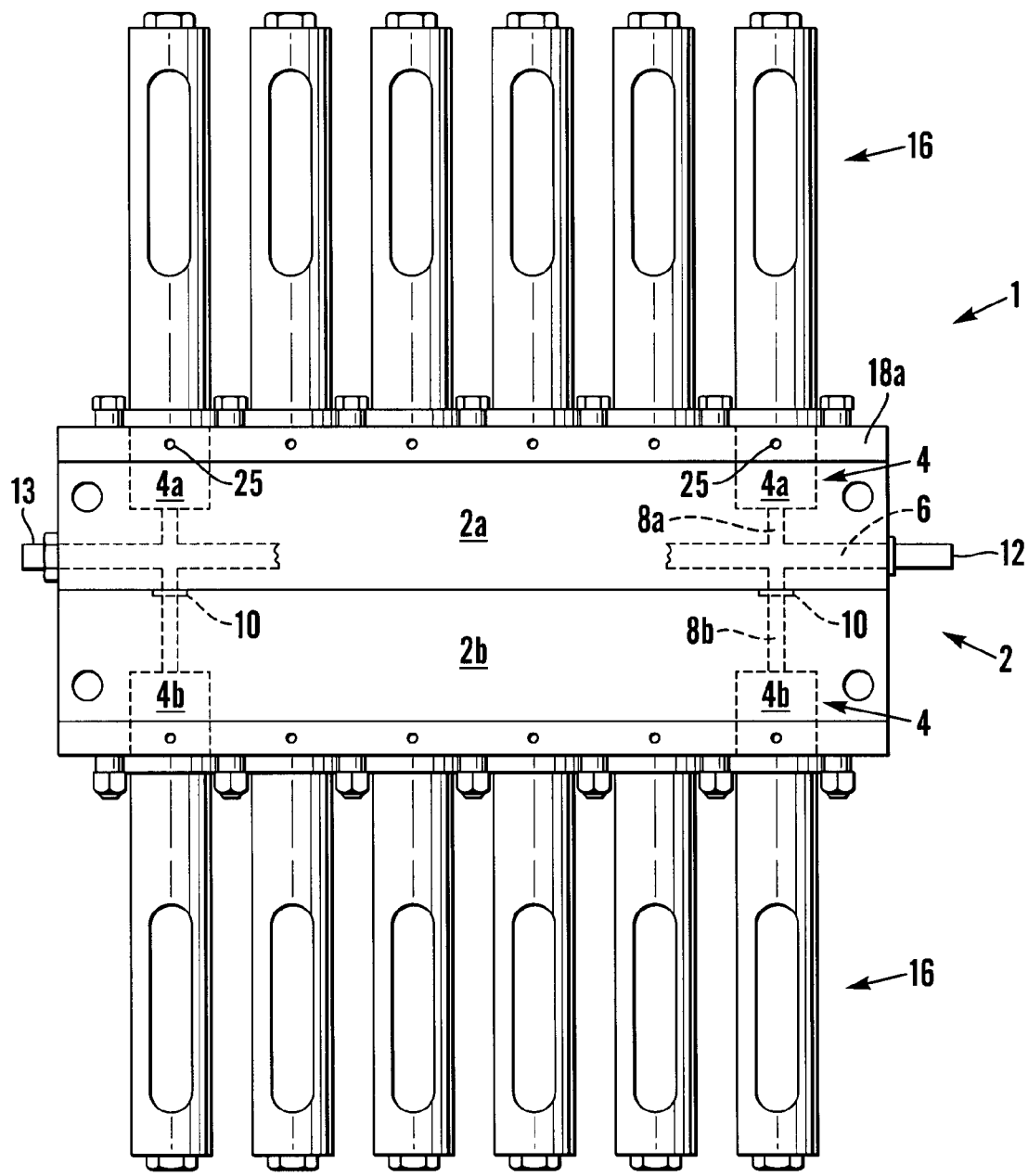
FIG. 1 is a plan view of stress device testing mounting apparatus according to the invention.
Figure 2:
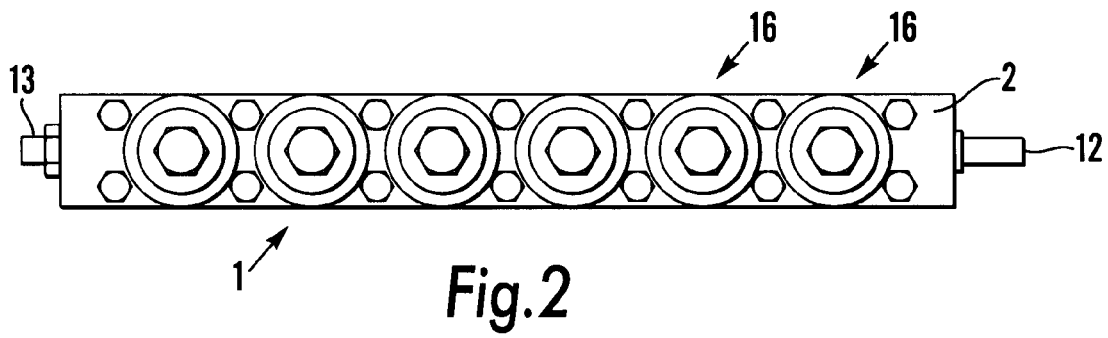
FIG. 2 is a side view of the apparatus shown in FIG. 1.

With reference to FIGS. 1 and 2, fatigue testing device mounting apparatus indicated generally at 1 comprises a cylinder block 2 including twelve cylinders 4. The block 2 is in two halves, 2a, 2b, divided longitudinally, with six cylinders 4a in a first half 2a and the other six cylinders 4b in corresponding positions in a second half 2b, so that the cylinders 4a are in axial alignment with the cylinders 4b. The two cylinder block halves 2a, 2b are machined from metal and held together by transversely extending bolts (not shown). Running longitudinally through the first cylinder block half 2a there is a bore 6 which has transverse branches 8a, 8b connecting the bore 6 to each of the cylinders 4a, 4b respectively. The branches 8b which cross the boundary between the two cylinder block halves 2a, 2b are sealed against leakage by o-ring seals 10 at the boundary.

At one end of the bore 6, there is a connector in the form of a projecting spigot 12 to which a source (not shown) of pressurised hydraulic fluid is connected. At the other end of the bore 6, there is a further projecting spigot 13 which can either be sealed or connected to pressure measuring equipment (not shown). Housed in each cylinder 4 is a piston 14 (not shown in FIGS. 1 and 2). The form of each piston 14a is determined by the nature of the stresses the piston 14a is designed to impart. What each piston 14a has in common is that its movement is determined by the pressure of the hydraulic fluid in the bore 6: As the pressure increases and more fluid is delivered from the bore 6 to each cylinder 4 each piston 14 will be urged away from the bore 6.

Figure 3:
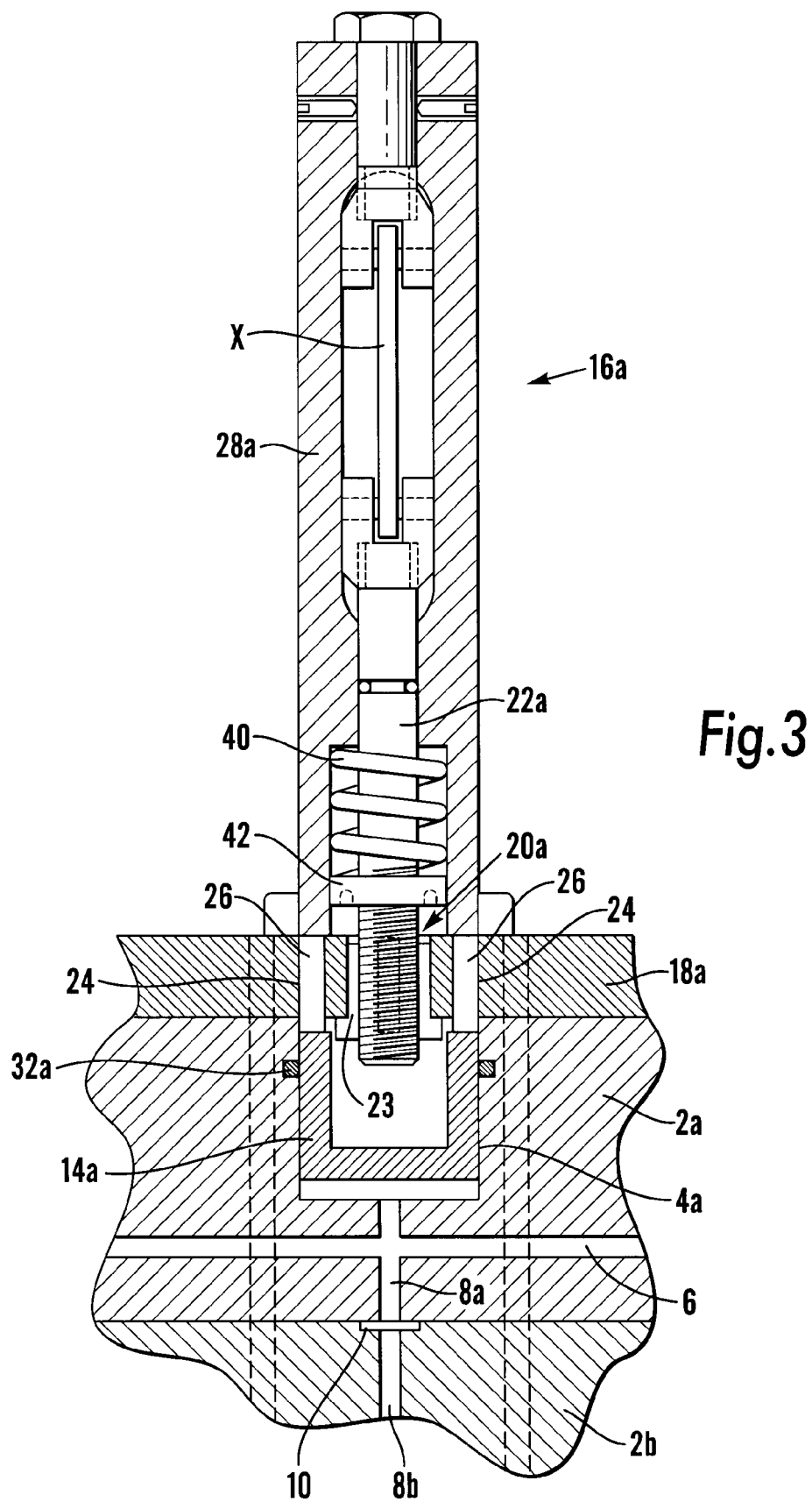
FIG. 3 is a partial cross-sectional view of one type of cylinder and piston arrangement found in the apparatus shown in FIG. 1.

With reference also to FIG. 3, tensile stress fatigue testing devices 16a are attached over each cylinder 4a in the first cylinder block half 2a. Each device 16a comprises an outer tubular housing 28a and a movable shaft 22a within the housing 28a. A specimen X for testing is attached between the housing 28a and the shaft 22a.

Affixed to the surface of the first cylinder block half 2a is a metal plate 18a. Extending through the plate 18a are a series of apertures 20a each coincident with an associated cylinder 4a. A cylindrical collar 23 is fitted in each aperture 20a and may be clamped fast by a grub screw 25 (see FIG. 1) with respect to the plate 18a. The collar 23 has an internal thread into which is screwed the shaft 22a of the device 16a. Also extending through the plate 18a, adjacent each aperture 20a, are holes 24 which slidably receive thrust pins 26. The holes 24 are aligned with the housing 28a of the device 16a, and the housing 28a abuts the pins 26 when the shaft 22a is screwed into the collar 23. The collar 22 may rotated and refastened with the grub screw 25 in a different position so as to alter the orientation of the specimen X.

Each cylinder 4a in the first cylinder block half 2a is for imparting tensile stress on the specimen X. Each piston 14a is generally U-shaped in cross-section and the edge of its cylindrical wall is in contact with the pins 26 which are longer than the holes 24. Thus, when the piston 14a is urged, as a result of an increase in the pressure of the hydraulic fluid, in the direction of the plate 18a, the pins 26 slide through the holes 24 and push the housing 28a away from the plate 18. As the specimen X is effectively fixed at one end via the shaft 22a to the plate 18a and at the other end to the housing 28a, the effect of pushing the housing 28a is to impart tensile stress on the specimen X.

The device 16a further includes a pre-tensioning spring 40 around the shaft 22a for applying an optional pre-load to the specimen X. The magnitude of the load is varied by adjustment of a collar 42 which is threadably received in the housing 28a. The pre-tensioning spring 40 may be calibrated or the load applied may be adjusted in conjunction with measuring apparatus.

Figure 4:
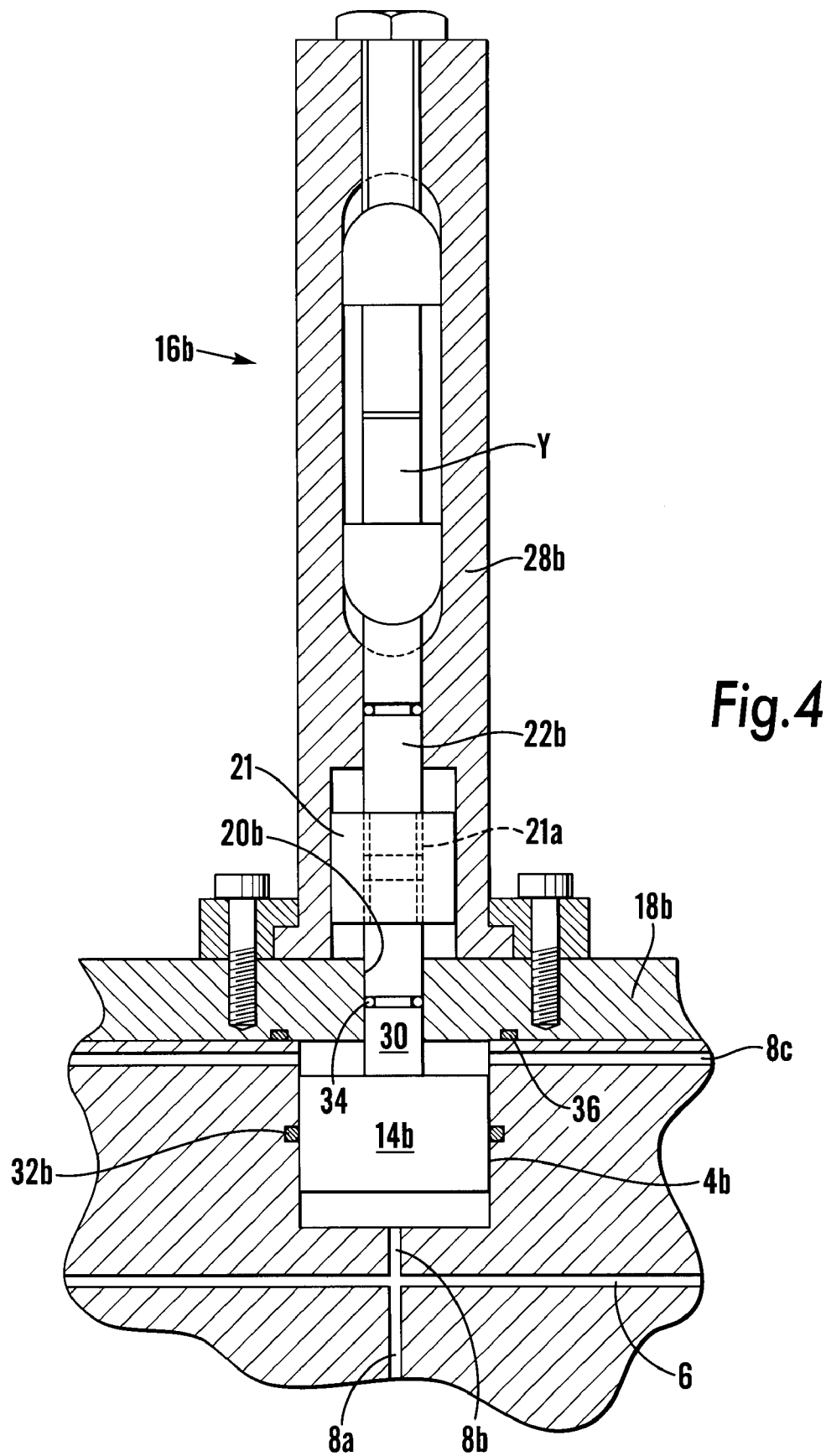
FIG. 4 is a partial cross-section of a further type of cylinder and piston arrangement found in the apparatus shown in FIG. 1.

With reference to FIG. 4, compressive stress fatigue testing devices 16b are attached over each cylinder 4b in the second cylinder block half 2b. The devices 16b comprise an outer tubular housing 28b and a movable shaft 22b within the housing 28b. A specimen Y for testing is attached between the housing 28b and the shaft 22b.

Affixed to the surface of the second cylinder block half 4b is a metal plate 18b. The housing 28b is bolted on to the plate 18b. Extending through the plate 18b are a series of apertures 20b each coincident with an associated cylinder 4b. One aperture 20b is shown in FIG. 4.

A stub 30 extending from the cylindrical piston 14b protrudes through the aperture 20b into an open end of the housing 28b. The end of stub 30 is externally threaded. The shaft 22b of each device 16b also protrudes into the open end of the housing 28b and is in axial alignment with the stub 30. The end of the shaft 22b is correspondingly externally threaded, and is thereby coupled to the stub 30 by means of an internally threaded collar 21. The ends of the stub 30 and shaft 22b, and their external threads are shown by the broken lines 21a.

Thus, when the piston 14b is lifted, as a result of an increase in the pressure of the hydraulic fluid, in the direction of the plate 18b, the shaft 22b is pushed away from the plate 18b. As the specimen Y is fixed at the end opposite to the shaft 22b to the housing 28b, the effect of pushing the shaft 22b is to impart compressive stress on the specimen Y.

Both forms of piston 14a, 14b are retained within their respective cylinders 4a, 4b by the plates 18a, 18b respectively and each piston 14a, 14b is sealed against hydraulic fluid leakage by a piston ring 32a, 32b seated in the cylinder wall. Therefore, any one of the devices 16a, 16b can be removed at any time, for instance when the specimen X, Y has failed, without significantly disturbing the hydraulic circuit of the apparatus or the operation of the remaining devices 16a, 16b.

More specifically, in the arrangement shown in FIG. 3, when the specimen X fails the piston 14a is urged out of the cylinder 4a until it is arrested by the plate 18a. When the piston 14a is in this position, the pins 26 are fully extended from the holes 24. Although the hydraulic circuit is not significantly disturbed, it can be restored to its pre-failure condition by removing the device 16a and fitting a replacement device 16a with a fresh specimen X. Alternatively, a collar, such as a washer of 10 mm thickness, (not shown) can be positioned over the pins 26 and secured by a bolt (not shown) which is screwed into the collar 23.

In the arrangement of FIG. 4, when the specimen Y fails under compression, the piston 14b is urged out of the cylinder 4b until it is arrested by the plate 18b. In this position, the stub 30 is filly extended through aperture 20b. In this arrangement, restoration of the hydraulic circuit to its pre-failure condition is achieved by fitting a replacement device 16b with a new specimen Y. Alternatively, a plate or suitable cap (not shown) can be positioned over the end of the stub 30 and bolted to the plate 18b.

With further reference to FIG. 4, optionally the second cylinder block half 2b is provided with further branches 8c, which communicate with the cylinder 4b on the side of piston 14b nearest the plate 18b. By diverting the hydraulic fluid along this additional branch 8b it is possible to push the piston 14b away from the plate 18b and thereby subject specimen Y not only to compressive stresses but also tensile stresses. However, additional seals 34, 36 between the stub 30 and the aperture walls and between the block 2b and the plate 18b respectively are also required to prevent leakage of hydraulic fluid.

Figure 5:
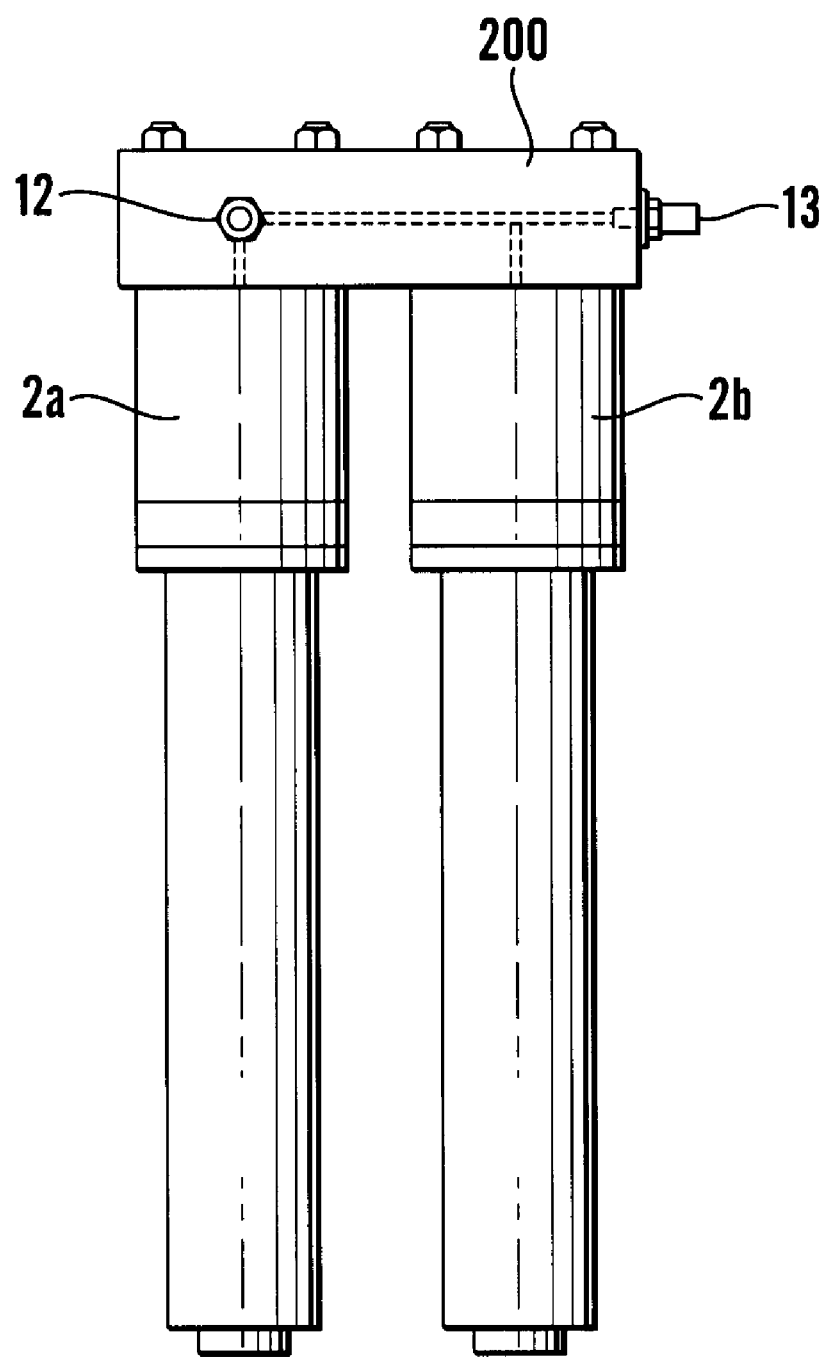
FIG. 5 is an end view of an alternative mounting apparatus to that shown in the earlier figures.

Variations in the stresses applied to the devices 16a, 16b are brought about by varying the pressure of the hydraulic fluid supplied from the source to the bore 6. Random variations are produced by monitoring a random event, for example when the apparatus is fitted to a vehicle (not shown), by measuring the reaction of an object, such as a ball confined in a tube, to the vehicles movements and by translating those reactions into a pressure value. Illustrated in FIG. 5 is an alternative mounting apparatus to that shown in FIGS. 1 and 2 (identical numbering used in FIG. 5 for parts common to FIGS. 1 and 2). The cylinder block halves 2a, 2b, rather than being arranged in an opposed fashion, are mounted in parallel, on the same side of a manifold 200. The bore 6 extends not only through the cylinder block halves 2a, 2b but also through the manifold 200 to a spigot 12 to which the source of pressurised hydraulic fluid is connected. The bore 6 also extends to a further spigot 13 for connecting measuring equipment.

In laboratory use, pressure may be generated using a hydraulic cylinder energised by an electric motor via a crank, connecting rod and spring (not shown). The spring characteristics may be chosen to ensure minimal changes in pressure, e.g. as a result of compliance in the system or displacement of fluid when one specimen fails. Such changes may be corrected automatically, e.g. using a controlled volume hydraulic fluid reservoir.

In in-situ vehicle use, the pressure characteristics may be maintained after specimen failure by various means, e.g. by ratchetting devices or by use of a vertical master cylinder the piston of which is subject to the forces generated by a connected mass oscillating in the vertical direction.

What is claimed is:

1. A stress testing apparatus for testing a plurality of test specimen comprising:

a cylinder block;

a plurality of cylinders formed in the cylinder block;

a plurality of pistons, each reciprocally mounted in a respective cylinder;

a plurality of stress testing devices releasably attached to the cylinder block, each stress testing device attached over a respective cylinder;

a test zone form ed within each stress testing device for securably receiving a test specimen;

first securing means disposed towards the remote end of each stress testing device, for securing a first end of a test specimen relative to the stress testing device;

second securing means disposed intermediate the remote end and the cylinder block, for securing a second end of the test specimen relative to the cylinder block; and thrust means disposed between each piston and stress testing device for transferring displacement of a piston to its associated stress testing device, to cause displacement of the stress testing device relative to the cylinder block and to load the first end of the test specimen relative to the second end.

2. A stress testing apparatus as set forth in claim 1, wherein the thrust means comprises a plurality of thrust pins.

3. A stress testing apparatus as set forth in claim 2, wherein a plate is affixed to the cylinder block, a plurality of first apertures extending through the plate, each coincident with an associated cylinder, and a plurality of second apertures received in the plate, each of which slidably receive a thrust pin.

4. A stress testing apparatus as set forth in claim 1, wherein the apparatus further comprises a source of pressurized fluid and means for conveying pressurized fluid from the source to each piston.

5. A stress testing apparatus as set forth in claim 4, wherein each piston is arranged so as to be retained in its respective cylinder, whether or not a device is mounted to interact with that piston, and sealing means provided in each cylinder wall to prevent leakage of pressurized fluid.

6. A stress testing apparatus as set forth in claim 4, wherein each stress testing device operates from a single source of pressurized hydraulic fluid.

7. A stress testing apparatus as set forth in claim 6, wherein the apparatus includes means for randomly varying the pressure of the fluid.

8. A stress testing apparatus as set forth in claim 7, wherein the pressure of the fluid is varied by a pump operated on a sinusoidal cycle.

9. A stress testing apparatus as set forth in claim 1, wherein the apparatus includes means for immersing the apparatus fully or partially in a liquid environment, for testing a specimen in that environment.

10. A stress testing apparatus as set forth in claim 1, wherein the apparatus comprises two cylinder blocks mounted in a back-to-back relationship, each cylinder block being connected to the source of pressurized fluid.

* * * * *